(12) United States Patent
Gates et al.

(10) Patent No.: US 8,828,364 B2
(45) Date of Patent: Sep. 9, 2014

(54) STRUCTURED SURFACTANT COMPOSITIONS

(75) Inventors: Ericka Gates, Mount Laurel, NJ (US);
Larry Hough, Philadelphia, PA (US);
Tobias Fütterer, Burlington, NJ (US)

(73) Assignee: Rhodia Operations, Aubervilliers (FR)

( * ) Notice: Subject to any disclaimer, the term of this patent is extended or adjusted under 35 U.S.C. 154(b) by 1497 days.

(21) Appl. No.: 12/077,834

(22) Filed: Mar. 21, 2008

(65) Prior Publication Data
US 2008/0233061 A1    Sep. 25, 2008

Related U.S. Application Data

(60) Provisional application No. 60/919,704, filed on Mar. 23, 2007.

(51) Int. Cl.
| | | |
|---|---|---|
| *A61K 8/33* | (2006.01) | |
| *A61K 8/42* | (2006.01) | |
| *A61K 8/46* | (2006.01) | |
| *A61Q 5/00* | (2006.01) | |
| *A61Q 13/00* | (2006.01) | |
| *C08K 5/06* | (2006.01) | |
| *C08K 5/20* | (2006.01) | |
| *C08K 5/36* | (2006.01) | |
| *A61K 8/20* | (2006.01) | |
| *A61Q 19/10* | (2006.01) | |
| *A61K 8/19* | (2006.01) | |
| *A61Q 5/02* | (2006.01) | |
| *C11D 17/00* | (2006.01) | |
| *C11D 1/94* | (2006.01) | |
| *C11D 1/65* | (2006.01) | |
| *A01N 25/30* | (2006.01) | |
| *A61K 8/45* | (2006.01) | |
| *C11D 3/04* | (2006.01) | |
| *A61K 8/02* | (2006.01) | |
| *A61K 8/44* | (2006.01) | |
| *C11D 1/88* | (2006.01) | |
| *C11D 1/52* | (2006.01) | |
| *C08K 5/41* | (2006.01) | |
| *C11D 1/14* | (2006.01) | |
| *C11D 1/29* | (2006.01) | |

(52) U.S. Cl.
CPC ... *A61K 8/42* (2013.01); *C11D 1/88* (2013.01); *A61K 8/20* (2013.01); *C08K 5/20* (2013.01); *A61K 2800/596* (2013.01); *C11D 1/528* (2013.01); *A61Q 19/10* (2013.01); *A61K 8/19* (2013.01); *A61Q 5/02* (2013.01); *C11D 1/523* (2013.01); *C11D 17/0026* (2013.01); *C11D 1/94* (2013.01); *C11D 1/652* (2013.01); *A01N 25/30* (2013.01); *A61K 8/466* (2013.01); *C08K 5/41* (2013.01); *A61K 8/45* (2013.01); *C11D 1/146* (2013.01); *C11D 3/046* (2013.01); *C11D 1/29* (2013.01); *A61K 8/0295* (2013.01); *A61K 8/442* (2013.01)

USPC ............................................................ 424/59

(58) Field of Classification Search
None
See application file for complete search history.

(56) References Cited

U.S. PATENT DOCUMENTS

| | | | |
|---|---|---|---|
| 4,001,394 A | 1/1977 | Fogel et al. | 424/70 |
| 4,069,347 A | 1/1978 | Mc Carthy et al. | 424/358 |
| 4,515,704 A | 5/1985 | Akred et al. | 252/135 |
| 4,659,497 A | 4/1987 | Akred et al. | 252/135 |
| 4,753,793 A | 6/1988 | Walton | 424/70 |
| 4,871,467 A | 10/1989 | Akred et al. | 252/135 |
| 4,964,874 A | 10/1990 | Saphakkul | 8/429 |
| 4,997,641 A | 3/1991 | Hartnett et al. | 424/70 |
| 5,114,706 A | 5/1992 | Duvel | 424/70 |
| 5,147,576 A | 9/1992 | Montague et al. | 252/174 |
| 5,358,667 A | 10/1994 | Bergmann | 252/547 |
| 5,397,493 A | 3/1995 | Potocki | 252/89.1 |
| 5,417,879 A | 5/1995 | Hall et al. | 252/174.17 |
| 5,520,839 A | 5/1996 | Hall et al. | 252/174.17 |
| 5,556,628 A | 9/1996 | Derian et al. | 424/401 |
| 5,602,092 A | 2/1997 | Repinec et al. | 510/434 |
| 5,612,307 A | 3/1997 | Chambers et al. | 510/406 |
| 5,650,384 A | 7/1997 | Gordon et al. | 510/159 |
| 5,716,920 A | 2/1998 | Glenn et al. | 510/159 |
| 5,776,883 A | 7/1998 | Vasudevan | 510/470 |
| 5,783,533 A | 7/1998 | Kensicher et al. | 510/119 |
| 5,792,472 A | 8/1998 | Roux et al. | 424/450 |
| 5,807,810 A | 9/1998 | Blezrd et al. | 507/103 |
| 5,851,978 A | 12/1998 | Shana'a | 510/417 |
| 5,858,938 A | 1/1999 | Glenn, Jr. et al. | 510/130 |
| 5,908,697 A | 6/1999 | Roux et al. | 428/402 |
| 5,916,575 A | 6/1999 | Mc Atee et al. | 424/401 |

(Continued)

FOREIGN PATENT DOCUMENTS

EP    0 719 857 A1    6/1988    ............. C11D 3/37
EP    0 295 021       12/1988

(Continued)

*Primary Examiner* — Ernst V Arnold

(57) ABSTRACT

A structured surfactant composition, comprising, based on 100 parts by weight of said composition,
(i) from greater than 0 to about 15 parts by weight of an alkyl ether sulfate surfactant,
(ii) from greater than 0 to about 15 parts by weight of an alkyl sulfate surfactant,
(iii) from greater than 0 to about 8 parts by weight of an alkanolamide surfactant,
(iv) from 0 to about 10 parts by weight of an amphoteric surfactant, provided that the total amount of components (i), (ii), (iii), and (iv) is greater than or equal to 5 parts by weight,
(v) an amount of electrolyte effective to, in combination with components (i), (ii), (ii), and (iv), provide a structured surfactant composition having an opaque visual appearance and exhibiting a yield strength of greater than 0 Pascals, and
(vi) water.

12 Claims, No Drawings

(56) References Cited

U.S. PATENT DOCUMENTS

| | | | |
|---|---|---|---|
| 5,925,364 A | 7/1999 | Ribler et al. | 424/401 |
| 5,929,019 A | 7/1999 | Puvvada et al. | 510/406 |
| 5,932,528 A | 8/1999 | Glenn, Jr. et al. | 510/130 |
| 5,935,915 A | 8/1999 | Gordon et al. | 510/130 |
| 5,952,285 A | 9/1999 | Hawkins | 510/405 |
| 5,964,692 A | 10/1999 | Blezard et al. | 516/59 |
| 6,066,328 A | 5/2000 | Ribier et al. | 424/401 |
| 6,066,607 A | 5/2000 | Gordon et al. | 510/130 |
| 6,066,608 A | 5/2000 | Glenn, Jr. | 510/159 |
| 6,077,816 A | 6/2000 | Puvvada et al. | 510/130 |
| 6,080,707 A | 6/2000 | Glenn, Jr. et al. | 510/130 |
| 6,080,708 A | 6/2000 | Glenn, Jr. et al. | 510/130 |
| 6,174,846 B1 | 1/2001 | Villa | 510/159 |
| 6,174,938 B1 | 1/2001 | Miller et al. | 523/164 |
| 6,177,390 B1 | 1/2001 | Guskey et al. | 510/119 |
| 6,177,396 B1 | 1/2001 | Clapperton et al. | 510/405 |
| 6,194,364 B1 | 2/2001 | Glenn, Jr. | 510/130 |
| 6,200,937 B1 | 3/2001 | Brennan et al. | 510/119 |
| 6,235,275 B1 | 5/2001 | Chen et al. | 424/70.1 |
| 6,280,758 B1 | 8/2001 | Warren et al. | 424/404 |
| 6,287,583 B1 | 9/2001 | Warren et al. | 424/404 |
| 6,325,995 B1 | 12/2001 | El-Nokaly et al. | 424/64 |
| 6,358,497 B2 | 3/2002 | Parry et al. | 424/62 |
| 6,395,690 B1 | 5/2002 | Tsaur | 510/130 |
| 6,416,768 B1 | 7/2002 | Ravaux et al. | 424/401 |
| 6,426,326 B1 | 7/2002 | Mitra et al. | 510/130 |
| 6,432,420 B2 | 8/2002 | Ellis et al. | 424/401 |
| 6,444,629 B1 | 9/2002 | Elliott et al. | 510/131 |
| 6,479,446 B1 | 11/2002 | Sherry et al. | 510/238 |
| 6,506,391 B1 | 1/2003 | Biatry | 424/401 |
| 6,534,456 B2 | 3/2003 | Hayward et al. | 510/130 |
| 6,534,457 B2 | 3/2003 | Mitra | 510/130 |
| 6,673,755 B2 | 1/2004 | Wei et al. | 510/130 |
| 6,682,723 B2 | 1/2004 | Parry et al. | 424/62 |
| 2002/0009425 A1 | 1/2002 | Cannell et al. | 424/70.23 |
| 2002/0012647 A1 | 1/2002 | Cannell et al. | 424/70.23 |
| 2002/0028755 A1 | 3/2002 | Van Dijk et al. | 510/392 |
| 2002/0034489 A1 | 3/2002 | Wiegland et al. | 424/70.24 |
| 2002/0119113 A1 | 8/2002 | Ellis et al. | 424/70.22 |
| 2003/0083210 A1 | 5/2003 | Goldberg et al. | 510/130 |
| 2003/0171231 A1 | 9/2003 | Shana'a et al. | 510/130 |
| 2003/0180246 A1 | 9/2003 | Frantz et al. | 424/70.21 |
| 2003/0190302 A1 | 10/2003 | Frantz et al. | 424/70.24 |
| 2005/0020468 A1* | 1/2005 | Frantz et al. | 510/424 |
| 2005/0201965 A1 | 9/2005 | Kuhlman et al. | 424/70.11 |
| 2006/0040837 A1 | 2/2006 | Frantz et al. | 510/130 |
| 2006/0094628 A1 | 5/2006 | Wei et al. | 510/417 |
| 2006/0135627 A1 | 6/2006 | Frantz et al. | 516/67 |
| 2007/0248562 A1* | 10/2007 | Berry et al. | 424/70.24 |
| 2008/0095733 A1 | 4/2008 | Griffin et al. | 424/70.19 |
| 2008/0233061 A1 | 9/2008 | Gates et al. | 424/59 |
| 2009/0048139 A1 | 2/2009 | Chen et al. | 510/416 |

FOREIGN PATENT DOCUMENTS

| | | | |
|---|---|---|---|
| EP | 0 346 993 | 12/1989 | |
| EP | 0 472 089 | 2/1992 | C09B 67/40 |
| EP | 0 504 159 B1 | 9/1992 | |
| EP | 0 506 695 | 10/1992 | C11D 3/386 |
| EP | 0 684 982 | 2/1993 | |
| EP | 0 530 708 | 3/1993 | |
| EP | 0 586 275 | 3/1994 | A61K 7/00 |
| EP | 0 771 188 B1 | 7/1994 | A61K 7/50 |
| EP | 0 419 164 | 11/1994 | A61K 7/00 |
| EP | 0 414 549 | 12/1994 | |
| EP | 0 659 205 | 6/1995 | C11D 1/83 |
| EP | 0 430 602 | 9/1995 | C10M 173/02 |
| EP | 0 691 399 | 1/1996 | C11D 17/00 |
| EP | 0 796 614 | 9/1997 | A61K 7/50 |
| EP | 0 796 615 | 9/1997 | A61K 7/50 |
| EP | 0 825 200 A1 | 2/1998 | C08F 2/24 |
| EP | 0 839 023 B1 | 5/1998 | A61K 7/50 |
| EP | 1 011 625 B1 | 6/2000 | A61K 7/48 |
| EP | 1 027 878 A1 | 8/2000 | A61K 7/00 |
| EP | 0 829 530 B1 | 12/2000 | C11D 1/83 |
| EP | 1 080 714 A2 | 3/2001 | A61K 7/06 |
| FR | 2771635 | 6/1999 | A61K 9/127 |
| GB | 2 057 533 A | 4/1981 | E21B 43/22 |
| GB | 2 292 155 A | 2/1996 | C11D 1/86 |
| GB | 2 355 015 A | 4/2001 | C11D 17/00 |
| WO | WO 9602224 A1 | 2/1996 | A61K 7/00 |
| WO | WO 96/10625 | 4/1996 | C11D 17/00 |
| WO | WO 97/11145 | 3/1997 | C11D 3/37 |
| WO | WO 98/01171 | 1/1998 | A61M 5/315 |
| WO | WO 98/13022 | 4/1998 | A61K 7/50 |
| WO | WO 99/09947 | 3/1999 | A61K 7/48 |
| WO | WO 99/09948 | 3/1999 | A61K 7/48 |
| WO | WO 99/09950 | 3/1999 | A61K 7/48 |
| WO | WO 99/09951 | 3/1999 | A61K 7/48 |
| WO | WO 99/20243 | 4/1999 | A61K 7/48 |
| WO | WO 99/27907 | 6/1999 | A61K 9/127 |
| WO | WO 00/36079 | 6/2000 | |
| WO | WO00/42985 | 7/2000 | A61K 7/48 |
| WO | WO 00/54749 | 9/2000 | A61K 9/127 |
| WO | WO 01/00778 A1 | 1/2001 | C11D 17/00 |
| WO | WO 01/00779 A1 | 1/2001 | C11D 17/00 |
| WO | WO 01/00780 A1 | 1/2001 | |
| WO | WO 01/05932 A1 | 1/2001 | C11D 17/00 |
| WO | WO 01/24807 A1 | 4/2001 | A61K 35/78 |
| WO | WO 01/70193 A2 | 9/2001 | A61K 7/50 |
| WO | WO 01/70926 A1 | 9/2001 | C11D 17/00 |
| WO | WO 02/05758 A2 | 1/2002 | A61K 7/00 |
| WO | WO 02/090477 A2 | 11/2002 | |
| WO | WO 03/055455 A1 | 7/2003 | A61K 7/075 |

* cited by examiner

STRUCTURED SURFACTANT COMPOSITIONS

This application claims the benefit of U.S. Provisional Patent Application Ser. No. 60/919,704, filed Mar. 23, 2007.

FIELD OF THE INVENTION

This invention relates to surfactant compositions, more particularly to structured surfactant compositions.

BACKGROUND OF THE INVENTION

Structured surfactant compositions are liquid crystalline compositions that are useful in home care applications such as liquid detergents, laundry detergents, hard surface cleansers, dish wash liquids, and personal care formulations such as shampoos, body wash, hand soap, lotions, creams, conditioners, shaving products, facial washes, baby care formulations, skin treatments. Surfactants in the structured surfactant compositions exist in the form of lamellar phases that are planar and/or in the form of spherulites. Commonly, the surfactant phase is present as spherulites, i.e., lamellar droplets, dispersed in the aqueous phase. Spherulites consist of an onion-like configuration of concentric bi-layers of surfactant molecules, between which is trapped water or electrolyte solution. Exclusively planar lamellar surfactant phases or exclusively spherulite lamellar surfactant phases or the combination of both forms can co-exist in the same composition. Structured surfactant compositions are typically pumpable, non-Newtonian compositions that have the capacity physically to suspend water insoluble particles by virtue of the presence of these lamellar surfactant phases.

What is needed is a way to efficiently produce such lamellar surfactant phases at reduced cost.

SUMMARY OF THE INVENTION

In a first aspect, the present invention is directed to a structured surfactant composition, comprising, based on 100 parts by weight of said composition,
(i) from greater than 0 to about 15 pbw of an alkyl ether sulfate surfactant,
(ii) from greater than 0 to about 15 pbw of an alkyl sulfate surfactant,
(iii) from greater than 0 to about 8 pbw of an alkanolamide surfactant,
(iv) from 0 to about 10 pbw of an amphoteric surfactant, provided that the total amount of components (i), (ii), (iii), and (iv) is greater than or equal to 5 pbw,
(v) an amount of electrolyte effective to, in combination with components (i), (ii), (ii), and (iv), provide a structured surfactant composition having an opaque visual appearance and exhibiting a yield strength of greater than 0 Pascals, and
(vi) water.

In a second aspect, the present invention is directed to composition, comprising, in each case based on 100 pbw of the composition:
(a) from about 50 to about 99 pbw of an aqueous structured surfactant phase, said structured surfactant phase comprising:
  (i) from greater than 0 to about 15 pbw of an alkyl ether sulfate surfactant,
  (ii) from greater than 0 to about 15 pbw of an alkyl sulfate surfactant,
  (iii) from greater than 0 to about 8 pbw of an alkanolamide surfactant,
  (iv) from 0 to about 10 pbw of an amphoteric surfactant, provided that the total amount of components (i), (ii), (iii), and (iv) is greater than or equal to 5 pbw
  (v) an amount of electrolyte effective to, in combination with components (i), (ii), (ii), and (iv), provide a structured surfactant composition having an opaque visual appearance and exhibiting a yield strength of greater than 0 Pascals, and
  (vi) water, and
(b) from about 1 to about 50 pbw of a discontinuous water insoluble or partially water soluble phase dispersed in the aqueous structured surfactant phase.

DETAILED DESCRIPTION OF INVENTION AND PREFERRED EMBODIMENTS

As used herein, the term "surfactant" means a compound that reduces surface tension when dissolved in water.

Except when expressly stated otherwise, all the components of formulations throughout the specification are expressed in parts by weight ("pbw") and are based on 100 pbw of the structured surfactant composition.

As referred to herein, "lamellar surfactant phases" are phases which comprise a plurality of stacked bilayers of surfactant separated by a liquid medium. Lamellar phases are typically pourable, non-Newtonian, anisotropic compositions that are cloudy looking and exhibit a characteristic "smeary" appearance on flowing. Lamellar phases can exist in several different forms, including layers of parallel sheets, each sheet of which is a bilayer of surfactant, and spherulites formed from layers of concentric spherical shells, each shell of which is a bilayer of surfactant. The spherulites are typically between 0.1 and 50 microns in diameter and so differ fundamentally from micelles.

The composition of the present invention comprises an ordered liquid crystal phase, typically a lamellar liquid crystal phase, more typically a spherulitic lamellar liquid crystal phase, and exhibits, on visual inspection, an opaque appearance due to the presence of the ordered liquid crystal phase.

As used herein, the term "opaque" means not completely transparent to light and ranges from a hazy translucent appearance through a turbid appearance to a uniform, saturated white appearance. In one embodiment, the structured surfactant compound of the present invention ranges from a turbid appearance to a uniform, saturated white appearance.

The ordered liquid crystal phase, alone or more typically interspersed with an aqueous phase, provides a rheology which is sufficient, when the system is at rest, to immobilize any suspended particles, but which is sufficiently low to allow the system to be pumped like a normal liquid. Such systems may display very low apparent viscosities when stirred, pumped or poured and yet be capable of maintaining particles, sometimes of millimeter or larger size, in suspension.

In one embodiment, the composition of the present invention exhibits shear-thinning viscosity. As used herein in reference to viscosity, the terminology "shear-thinning" means that such viscosity decreases with an increase in shear rate. Shear-thinning may be characterized as a "non-Newtonian" behavior, in that it differs from that of a classical Newtonian fluid, for example, water, in which viscosity is not dependent on shear rate.

As used herein, "yield strength" refers to the magnitude of the applied force required to induce the composition to flow. In one embodiment, the composition exhibits a yield strength of greater than 0.1 Pascals ("Pa"), more typically from about 1 to about 100 Pa, and even more typically from about 1 to about 10 Pa, as determined by measurements using a controlled stress/strain rheometer at two or more shear rates.

In one embodiment, the composition of the present invention is capable of suspending water insoluble or partially water-soluble components.

As used herein in reference to a component of an aqueous composition, the terminology "water insoluble or partially water-soluble components" means that the component is present in the aqueous composition at a concentration above the solubility limit of the component so that, in the case of a water insoluble component, the component remains substantially non-dissolved in the aqueous composition and, in the case of a partially water-soluble component, at least a portion of such component remains undissolved in the aqueous composition. The water insoluble or partially water-soluble components may, for example, be in the form of solid particles, of continuous or discontinuous liquid phases, such as oil droplets, or of discontinuous gas phases, such as air bubbles.

As used herein, characterization of an aqueous composition as "capable of suspending", or as being "able of suspend" water insoluble or partially water-soluble components means that the composition substantially resists flotation of such components in the composition or sinking of such components in such composition so that such components appear to be neutrally buoyant in such composition and remain at least substantially suspended in such composition under the anticipated processing, storage, and use conditions for such aqueous composition. The ability to suspend water insoluble or partially water-soluble components is one manifestation of the non-zero yield strength of the present invention, that is, the resistance of the structured surfactant composition of the present invention to deformation at low stresses is sufficient to balance the gravitational forces acting on water insoluble or partially water-soluble components, so that the components remain suspended in the structured surfactant composition.

The structured surfactant composition of the present invention comprises, based on 100 pbw of the composition, from about 40 to about 90 pbw, more typically from about 50 to about 85 pbw, water.

As used herein, the terminology "$(C_x$-$C_y)$" in reference to an organic group, wherein x and y are each integers, indicates that the group may contain from x carbon atoms to y carbon atoms per group.

As used herein, the term "alkyl" means a monovalent saturated straight chain or branched hydrocarbon group, more typically a monovalent saturated $(C_8$-$C_{18})$ hydrocarbon group, such as octyl, nonyl, decyl undecyl, dodecyl, tridecyl, tetradecyl, pentadecyl, hexadecyl, heptadecyl, octadecyl, methyldodecyl, ethylundecyl, or dimethylundecyl. Alkyl groups are also referred to by their respective trivial names, for example, "lauryl" and "dodecyl" each refer to $C_{12}$ alkyl.

As used herein, the term "alkenyl" means a monovalent unsaturated straight chain or branched hydrocarbon group, more typically a monovalent unsaturated $(C_8$-$C_{18})$ hydrocarbon group, such as octenyl, nonenyl, decenyl undecenyl, dodecenyl, tridecenyl, tetradecenyl, pentadecenyl, hexadecenyl, heptadecenyl, octadecenyl, methyldodecenyl, ethylundecenyl, or dimethylundecenyl.

As used herein, the term "cation" means a cation that is acceptable for use in a personal care composition, including sodium, potassium, lithium, calcium, magnesium, and ammonium cations, as well as $(C_1$-$C_6)$alkylammonium and $(C_1$-$C_6)$alkoxylammonium cations, such as isopropylammonium, monoethanolammonium, diethanolammonium, and triethanolammonium cation. Ammonium salts are generally more soluble than the sodium salts. Mixtures of the above cations may be used.

In one embodiment, the composition of the present invention comprises, based on 100 pbw of the composition, from about 0.5 to about 10 pbw, more typically from about 1 to about 8 pbw, of the alkyl ether sulfate surfactant.

In one embodiment, the alkyl ether sulfate surfactant comprises one or more compounds according to structure (I):

wherein:
$R^1$ is $(C_8$-$C_{18})$alkyl or $(C_8$-$C_{18})$alkenyl, more typically $(C_{10}$-$C_{14})$alkyl,
m is 2, 3, or 4,
n is an integer of from 1 to about 7, more typically from 1 to 8, even more typically from 1 to 6,
$X^+$ is a cation.

In one embodiment, $R^1$ is a branched $(C_8$-$C_{18})$alkyl group or a $(C_8$-$C_{18})$alkenyl group, more typically a branched $(C_{10}$-$C_{16})$alkyl group, such as tridecyl.

Suitable branched alkyl groups include methyldecyl groups, methylundecyl groups, methyldodecyl groups, ethyldecyl groups, ethylundecyl groups, and ethyldodecyl groups, such as for example, 1-methyldecyl, 1-methylundecyl, 1-methyldodecyl, 1-ethyldecyl, 1-ethylundecyl, and 1-ethyldodecyl.

In one embodiment, m is 2 or 3, more typically 2.

In one embodiment, n is 1, 2, 3, or 4. As used herein, modifying an alkyl or alkenyl group with the suffix "eth" generally indicates the addition of one or more ethylene oxide units, for example, trideceth refers to an ethoxylated tridecyl group, and the suffix "-n", wherein n is an integer, indicates the number of such ethylene oxide units per group, for example "trideceth-3" indicates an ethoxylated tridecyl group with 3 ethylene oxide units per tridecyl group.

In one embodiment, the alkyl ether sulfate surfactant comprises one or more compounds selected from sodium laureth sulfates, potassium laureth sulfates, magnesium laureth sulfates, ammonium laureth sulfates, monoethanolamine laureth sulfates, diethanolamine laureth sulfates, triethanolamine laureth sulfates, sodium trideceth sulfates, magnesium trideceth sulfates, ammonium trideceth sulfates, monoethanolamine trideceth sulfates, diethanolamine trideceth sulfates, and triethanolamine trideceth sulfates. sodium oleth sulfates, potassium oleth sulfates, magnesium oleth sulfates, ammonium oleth sulfates, monoethanolamine oleth sulfates, diethanolamine oleth sulfates, triethanolamine oleth sulfates.

In one embodiment, the alkyl ether sulfate surfactant comprises one or more branched alkylether sulfate selected from sodium trideceth-1 sulfate, potassium trideceth-1 sulfate, and ammonium trideceth-1 sulfate, sodium trideceth-2 sulfate, potassium trideceth-2 sulfate, and ammonium trideceth-2 sulfate, sodium trideceth-3 sulfate, potassium trideceth-3 sulfate, and ammonium trideceth-3 sulfate, sodium trideceth-4 sulfate, potassium trideceth-4 sulfate, and ammonium trideceth-4 sulfate.

In one embodiment, the composition of the present invention comprises, based on 100 pbw of the composition, from about 1.5 to about 12 pbw, more typically from about 3 to about 10 pbw, of the alkyl sulfate surfactant.

In one embodiment, the alkyl sulfate surfactant comprises one or more compounds according to structure (II):

wherein:
$R^2$ is $(C_8$-$C_{18})$alkyl or $(C_8$-$C_{18})$alkenyl, and
$X^+$ is a cation.

In one embodiment, $R^2$ is dodecyl, tridecyl, or oleyl.

In one embodiment, the alkyl sulfate surfactant comprises one or more compounds selected from sodium lauryl sulfate, potassium lauryl sulfate, magnesium lauryl sulfate, ammonium lauryl sulfate, monoethanolamine lauryl sulfate, diethanolamine lauryl sulfate, triethanolamine lauryl sulfate, sodium tridecyl sulfate, potassium tridecyl sulfate, magnesium tridecyl sulfate, ammonium tridecyl sulfate, monoethanolamine tridecyl sulfate, diethanolamine tridecyl sulfate, triethanolamine tridecyl sulfate, sodium oleyl sulfate, potassium oleyl sulfate, magnesium oleyl sulfate, ammonium oleyl sulfate, monoethanolamine oleyl sulfate, diethanolamine oleyl sulfate, triethanolamine oleyl sulfate.

In one embodiment, the composition of the present invention comprises, based on 100 pbw of the composition, from about 0.5 to about 6 pbw, more typically from about 1 to about 4 pbw, of the alkanolamide.

In one embodiment, the alkanolamide comprises one or more compounds according to structure (III):

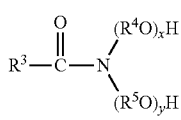

(III)

wherein:
 $R^3$ is ($C_5$-$C_{24}$) saturated or unsaturated, straight chain or branched aliphatic group,
 $R^4$ and R5 are the same or different, $C_2$-$C_4$ straight chain or branched aliphatic groups,
 x is an integer from 0 to 10, y is an integer from 1 to 10, and the sum of x and y is less than or equal to 10.

Suitable alkanolamides include aliphatic acid alkanolamides, such as cocamide MEA (coco monoethanolamide) and cocamide MIPA (coco monoisopropanolamide), cocamide DEA (coco diethanolamide, lauramide MEA (lauryl monoethanolamide), lauramide DEA (lauryl diethanolamide), and alkoxylated alkanolamides, such as PEG-5 cocamide MEA (compound according to structure (III) above (that is, a compound wherein $R^3$ is ($C_{12}$-$C_{12}$)alkyl, $R^4$ and $R^5$ are each $C_2H_4$, and x+y=5), as well as mixture of any of the above.

In one embodiment, the total amount of components (i), (ii), (iii), and (iv) is greater than or equal to about 10 pbw, more typically greater than or equal to about 15 pbw, of the composition, The electrolyte component of the composition of the present invention induces formation of a lamellar liquid crystal surfactant phase, from which the opaque visual appearance and the non-zero yield strength of the structured surfactant composition of the present invention arise.

In one embodiment, the structured surfactant composition of the present invention further comprises, based on 100 pbw of the structured surfactant composition, up to about 20 pbw, more typically from about 0.1 to about 15 pbw, and still more typically from about 0.5 to about 10 pbw, of an electrolyte.

Suitable electrolytes include organic salts, inorganic salts, and mixtures thereof, as well as polyelectrolytes, such as uncapped polyacrylates, polymaleates, or polycarboxylates, lignin sulfonates or naphthalene sulfonate formaldehyde copolymers. The electrolyte typically comprises a salt having a cationic component and an anionic component. Suitable cations may be monovalent or multivalent, may be organic or inorganic, and include, for example, sodium, potassium, lithium, calcium, magnesium, cesium, and lithium cations, as well as mono-, di- tri- or quaternary ammonium or pyridinium cation. Suitable anions may be a monovalent or multivalent, may be organic or inorganic, and include, for example, chloride, sulfate, nitrate, nitrite, carbonate, citrate, cyanate acetate, benzoate, tartarate, oxalate, phosphate, and phosphonate anions. Suitable electrolytes include, for example, salts of multivalent anions with monovalent cations, such as potassium pyrophosphate, potassium tripolyphosphate, and sodium citrate, salts of multivalent cations with monovalent anions, such as calcium chloride, calcium bromide, zinc halides, barium chloride, and calcium nitrate, and salts of monovalent cations with monovalent anions, such as sodium chloride, potassium chloride, potassium iodide, sodium bromide, ammonium bromide, alkali metal nitrates, and ammonium nitrates. Electrolyte may be added as a separate component or in combination with other components of the composition of the present invention.

In one embodiment, the electrolyte comprises NaCl, $NH_4Cl$, or a mixture thereof. The use of $NH_4Cl$ as at least a portion of the electrolyte component of the composition of the present invention has been found to offer improved efficiency, that is, compared to other electrolytes, a smaller amount of $NH_4Cl$ is needed to, in combination with the other components of the composition, provide a structured surfactant composition having an opaque visual appearance and exhibiting a yield strength of greater than 0 Pascals. In one embodiment, the electrolyte comprises $NH_4Cl$.

In one embodiment, the composition of the present invention further comprises an amphoteric surfactant.

In one embodiment, the composition of the present invention comprises, based on 100 pbw of the composition, from about 1 to about 8 pbw, more typically from about 2 to about 6 pbw, of an amphoteric surfactant.

Suitable amphoteric surfactants include for example, derivatives of aliphatic secondary and tertiary amines in which the aliphatic radical can be straight chain or branched and wherein one of the aliphatic substituents contains from about 8 to about 18 carbon atoms and one contains an anionic water-solubilizing group as well as mixtures thereof. Specific examples of suitable amphoteric surfactants include the alkali metal, alkaline earth metal, ammonium or substituted ammonium salts of alkyl amphocarboxy glycinates and alkyl amphocarboxypropionates, alkyl amphodipropionates, alkyl amphodiacetates, alkyl amphoglycinates, and alkyl amphopropionates, as well as alkyl iminopropionates, alkyl iminodipropionates, and alkyl amphopropylsulfonates, such as for example, cocoamphoacetate cocoamphopropionate, cocoamphodiacetate, lauroamphoacetate, lauroamphodiacetate, lauroamphodipropionate, lauroamphodiacetate, cocoamphopropyl sulfonate caproamphodiacetate, caproamphoacetate, caproamphodipropionate, and stearoamphoacetate.

In one embodiment, the amphoteric surfactant the amphoteric surfactant comprises one or more compounds selected from compounds according to structures (IV) and (V):

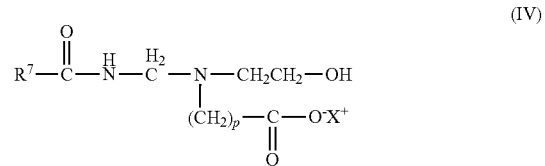

(IV)

-continued

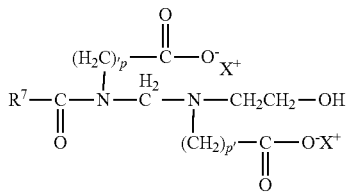
(V)

wherein:
$R^6$ is $(C_1-C_{18})$aliphatic,
p is 2 or 3,
$R^7$ is $(C_1-C_{18})$aliphatic,
p' is 2 or 3, and
each $X^+$ is independently a cation.

In one embodiment, $R^6$ is $(C_{10}-C_{14})$alkyl, more typically decyl, dodecyl, or a mixture of dodecyl and tetradecyl.

In one embodiment, $R^7$ is $(C_{10}-C_{14})$alkyl, more typically decyl, dodecyl, or a mixture of dodecyl and tetradecyl.

In one embodiment, the amphoteric surfactant comprises one or more of sodium lauroamphoacetate, disodium lauroamphodiacetate, sodium lauroamphopropionate, disodium lauroamphodipropionate sodium cocoamphoacetate, disodium cocoamphodiacetate, sodium capryloamphopropionate, and disodium capryloamphodiacetate.

In one embodiment, a structured surfactant composition, comprising, based on 100 pbw of said composition:
(i) from greater than 0 to about 15 pbw, more typically from about 0.5 to about 10 pbw, and still more typically from about 1 to about 8 pbw, of an alkyl ether sulfate surfactant comprising one or more compounds according to structure (I)

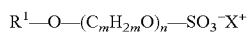 (I)

wherein
$R^1$ is $(C_8-C_{18})$alkyl,
m is 2 or 3,
n is an integer of from 1 to about 5 and
$X^+$ is a cation.
(ii) from greater than 0 to about 15 pbw, more typically from about 1.5 to about 12 pbw, and still more typically from about 3 to about 10 pbw, of an alkyl sulfate surfactant comprising one or more compounds according to structure (II):

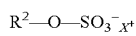 (II)

wherein:
$R^2$ is $(C_8-C_{18})$alkyl, and
$X^+$ is a cation.
(iii) from greater than 0 to about 10 pbw, more typically from about 0.5 to about 6 pbw, and still more typically from about 1 to about 4 pbw, of an alkanolamide surfactant comprising one or more compounds according to structure (III):

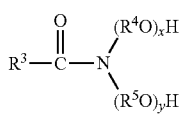 (III)

wherein:
$R^3$ is $(C_5-C_{24})$ saturated or unsaturated, straight chain or branched aliphatic group,
$R^4$ and R5 are the same or different, $C_2-C_4$ straight chain or branched aliphatic groups,
x is an integer from 0 to 10, y is an integer from 1 to 10, and the sum of x and y is less than or equal to 10, and
(iv) from 0 to about 10 pbw, more typically from about 1 to about 8 pbw, and still more typically from about 2 to about 6 pbw, of an amphoteric surfactant comprising one or more compounds selected from compounds according to structures (IV) and (V):

 (IV)

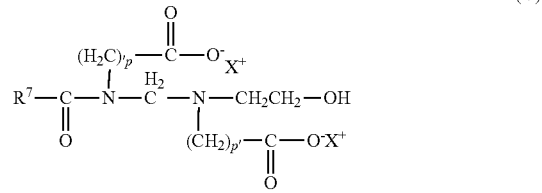 (V)

wherein:
$R^6$ is $(C_1-C_{18})$aliphatic,
p is 2 or 3,
$R^7$ is $(C_1-C_{18})$aliphatic,
p' is 2 or 3, and
each X+ is, independently a cation,
provided that the total amount of components (i), (ii), (iii), and (iv) is greater than or equal to 5 pbw, more typically greater than or equal to about 10 pbw, and still more typically greater than or equal to about 15 pbw, of the composition,
(v) an amount of electrolyte effective to, in combination with components (i), (ii), (ii), and (iv), provide a structured surfactant composition having an opaque visual appearance and exhibiting a yield strength of greater than 0 Pascals, and
(vi) water.

The composition may, optionally, further comprise up to about 30 pbw, more typically up to about 10 pbw, per 100 pbw of the composition of additional surfactants, including cationic surfactants, nonionic surfactants other than alkanolamides, zwitterionic surfactants, and mixtures thereof.

Suitable cationic surfactants are typically monocationic compounds, that is, having a single cationic site per molecule, and include quaternary ammonium compounds, such as cetyl trimethyl ammonium bromide (also known as CETAB or cetrimonium bromide), cetyl trimethyl ammonium chloride (also known as cetrimonium chloride), myristyl trimethyl ammonium bromide (also known as myrtrimonium bromide or Quaternium-13), stearyl dimethyl distearyidimonium chloride, dicetyl dimonium chloride, stearyl octyldimonium methosulfate, dihydrogenated palmoylethyl hydroxyethylmonium methosulfate, isostearyl benzylimidonium chloride, cocoyl benzyl hydroxyethyl imidazolinium chloride, dicetyl dimonium chloride and distearyldimonium chloride; isostearylaminopropalkonium chloride or olealkonium chloride; behentrimonium chloride; as well as mixtures thereof.

In one embodiment, the composition of the present invention is free of monocationic surfactants. In one embodiment, the composition of the present invention is free of cationic surfactants. In one embodiment, the composition of the present invention is free of cationic compounds other than a polycationic polymeric thickener, such as a cationic guar, as described below.

Suitable nonionic surfactants include amine oxides such lauramine oxide, cocamine oxide, stearamine oxide, stearamidopropylamine oxide, palmitamidopropylamine oxide, decylamine oxide, fatty alcohols such as decyl alcohol, lauryl alcohol, tridecyl alcohol, myristyl alcohol, cetyl alcohol, stearyl alcohol, oleyl alcohol, linoleyl alcohol and linolenyl alcohol, alkoxylated alcohols such as ethoxylated lauryl alcohol having an average of 5 ethylene oxide units per molecule, trideceth alcohols, fatty acids such as lauric acid, oleic acid, stearic acid, myristic acid, cetearic acid, isostearic acid, linoleic acid, linolenic acid, ricinoleic acid, elaidic acid, arichidonic acid, myristoleic acid, fatty acid esters such as propylene glycol isostearate, propylene glycol oleate, glyceryl isostearate, and glyceryl oleate, and mixtures thereof.

In one embodiment, the composition of the present invention is free of nonionic surfactants other than the alkanolamide component of the composition.

Suitable zwitterionic surfactants include alkyl betaines, such as cocodimethyl carboxymethyl betaine, lauryl dimethyl carboxymethyl betaine, lauryl dimethyl alpha-carboxyethyl betaine, cetyl dimethyl carboxymethyl betaine, lauryl bis-(2-hydroxy-ethyl)carboxy methyl betaine, stearyl bis-(2-hydroxy-propyl)carboxymethyl betaine, oleyl dimethyl gamma-carboxypropyl betaine, and lauryl bis-(2-hydroxypropyl)alpha-carboxyethyl betaine, amidopropyl betaines, and alkyl sultaines, such as cocodimethyl sulfopropyl betaine, stearyldimethyl sulfopropyl betaine, lauryl dimethyl sulfoethyl betaine, lauryl bis-(2-hydroxy-ethyl)sulfopropyl betaine, and alkylamidopropylhydroxy sultaines.

The structured surfactant composition of the present invention may optionally further comprise one or more preservatives, such as benzyl alcohol, methyl paraben, propyl paraben, or imidazolidinyl urea, and DMDM hydantoin, and may optionally further comprise one or more pH adjusting agents, such as citric acid, succinic acid, phosphoric acid, sodium hydroxide, or sodium carbonate.

In general, the structured surfactant composition is made by combining and mixing the anionic surfactant and water, adding the structuring agent, then adding the solvent, and optionally, adjusting the pH and/or adding a preservative. Alternately the solvent may be added with the anionic surfactant and the water. The structured surfactant composition can also be subjected to high shear mixing. As used herein, the term "high shear mixing" refers to mixing under high shear conditions, typically at a shear rate of greater than or equal to about 1,000 $s^{-1}$, more typically greater than or equal to about 3,500 $s^{-1}$ The structured surfactant composition may be subjected to a high shear mixing in known mixing equipment, such as, for example, a high shear mixer or a homogenizer.

In one embodiment, the pH of the structured surfactant composition of the present invention is from 4 to 8, more typically from 5 to 6.

The composition of the present invention is capable of suspending water-insoluble particles or partially water-soluble components, such as vegetable oils, hydrocarbon oils, silicone oils, solid particles, abrasives, and similar articles. The composition provides a means to include otherwise difficult to incorporate components in surfactant mixtures resulting in cosmetic preparations with multi-functional benefits including, in some cases, cleansing, moisturizing, improved skin feel, exfoliation/abrasion, novel appearance, or a combination of these benefits.

The ability of a composition to suspend water insoluble or partially water-soluble components is typically evaluated by mixing the composition with sufficient vigor to entrap air bubbles in the composition and then visually observing whether the air bubbles remain entrapped in the composition for a defined period of time, such as for example, 12 to 24 hours, under defined environmental conditions, such as for example, room temperature. In one embodiment, the composition of the present invention is capable of suspending air bubbles for at least 1 week, and more typically for at least 3 months. A composition that is capable of suspending air bubbles for at least 12 hours at room temperature is deemed to be generally capable of suspending water insoluble or partially water-soluble components in the composition under generally anticipated processing, storage, and use conditions for such composition. For components other than air, the result of the air suspension test should be confirmed by conducting an analogous suspension test using the component of interest. For unusually rigorous processing, storage and/or use conditions, more rigorous testing may be appropriate.

In one embodiment, the ability to suspend water insoluble or partially water-soluble components is evaluated under more rigorous conditions, that is, the mixed samples are visually evaluated after subjecting the samples to one or more freeze/thaw cycles, wherein each freeze/thaw cycle consists of 12 hours at $-10°$ C. and 12 hours at 25° C. In one embodiment, composition of the present invention remains capable of suspending air bubbles after one freeze/thaw cycle, more typically after 3 freeze/thaw cycles.

The composition of the present invention is useful in, for example, personal care applications, such as shampoos, body wash, hand soap, lotions, creams, conditioners, shaving products, facial washes, neutralizing shampoos, personal wipes, and skin treatments, and in home care applications, such as liquid detergents, laundry detergents, hard surface cleansers, dish wash liquids, toilet bowl cleaners, as well as other applications, such as oil field and agrochemical applications.

In one embodiment, the personal care composition of the present invention comprises one or more "benefit agents" that is, materials that provide a personal care benefit, such as moisturizing or conditioning, to the user of the personal care composition, such as, for example, emollients, oils, moisturizers, humectants, conditioners, polymers, vitamins, abrasives, UV absorbers, antimicrobial agents, anti-dandruff agents, fragrances, and/or appearance modifying additives, such as, for example, colored particles or reflective particles, which may be in the form of a solid, liquid, or gas and may be insoluble or are only partly soluble in the structured surfactant composition. Mixtures of the benefit agents may be used.

In one embodiment, the personal care composition of the present invention provides enhanced deposition of a benefit agent onto the skin or hair.

In one embodiment, the personal care composition according to the present invention comprises a humectant. Suitable humectants are those physiologically and cosmetically acceptable materials effective in attracting moisture to the epidermis and include, for example, ammonium lactate, sodium lactate, propylene glycol, butylene glycol, glycerin, diglycerin, honey, polyglycerylmethacrylate, lactic acid, hyaluronic acid, glucuronic acid, polyglucuronic acid, glutamic acid, glucuronolactone, sodium salt of 2-pyrrolidone-5-carboxylic acid ("sodium PCA"), panthenol, sorbitol, hydroxyethyl sorbitol, glucose, xylose, sodium aspartate, and sodium polyaspartate, urea, as well as mixtures of any of the foregoing. In one embodiment, the humectant comprises glycerin.

In one embodiment, the personal care composition of the present invention comprises, in each case based on 100 pbw of the composition:

(a) from about 50 to less than 100 pbw, more typically from about 70 to about 99 pbw, of an aqueous structured surfactant phase, said structured surfactant phase comprising:

(i) from greater than 0 to about 15 pbw, more typically from about 0.5 to about 10 pbw, and still more typically from about 1 to about 8 pbw, of an alkyl ether sulfate surfactant comprising one or more compounds according to structure (I)

$$R^1\text{—}O\text{—}(C_mH_{2m}O)_n\text{—}S_3^-X^+ \quad (I)$$

wherein
$R^1$ is $(C_8\text{-}C_{18})$alkyl,
m is 2 or 3,
n is an integer of from 1 to about 5 and
$X^+$ is a cation.

(ii) from greater than 0 to about 15 pbw, more typically from about 1.5 to about 12 pbw, and still more typically from about 3 to about 10 pbw, of an alkyl sulfate surfactant comprising one or more compounds according to structure (II):

$$R^2\text{—}O\text{—}SO_3^-{}_{X^+} \quad (II)$$

wherein:
$R^2$ is $(C_8\text{-}C_{18})$alkyl, and
$X^+$ is a cation.

(iii) from greater than 0 to about 10 pbw, more typically from about 0.5 to about 6 pbw, and still more typically from about 1 to about 4 pbw, of an alkanolamide surfactant comprising one or more compounds according to structure (III):

wherein:
$R^3$ is $(C_5\text{-}C_{24})$ saturated or unsaturated, straight chain or branched aliphatic group,
$R^4$ and R5 are the same or different, $C_2\text{-}C_4$ straight chain or branched aliphatic groups,
x is an integer from 0 to 10, y is an integer from 1 to 10, and the sum of x and y is less than or equal to 10, and (iv) from 0 to about 10 pbw, more typically from about 1 to about 8 pbw, and still more typically from about 2 to about 6 pbw, of an amphoteric surfactant comprising one or more compounds selected from compounds according to structures (IV) and (V):

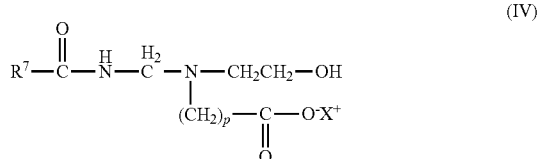

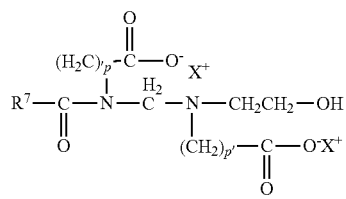

wherein:
$R^6$ is $(C_1\text{-}C_{18})$aliphatic,
p is 2 or 3,
$R^7$ is $(C_1\text{-}C_{18})$aliphatic,
p' is 2 or 3, and
each X+ is independently a cation,
provided that the total amount of components (i), (ii), (iii), and (iv) is greater than or equal to 5 pbw, more typically greater than or equal to about 10 pbw, and still more typically greater than or equal to about 15 pbw, of the composition, (v) an amount of electrolyte effective to, in combination with components (i), (ii), (ii), and (iv), provide a structured surfactant composition having an opaque visual appearance and exhibiting a yield strength of greater than 0 Pascals, and
(vi) water, and (b) from greater than 0 to about 50 pbw, more typically from about 1 to about 30 pbw of one or more benefit agents.

In one embodiment of the personal care composition of the present invention, the benefit agent comprises a humectant. In one embodiment, the benefit agent comprises, based on 100 pbw of the composition, from greater than 0 to about 25 pbw, more typically from about 0.5 to about 20 pbw, humectant.

In one embodiment of the personal care composition of the present invention, the benefit agent comprises one or more oils. In one embodiment, the benefit agent comprises, based on 100 pbw of the composition, from greater than 0 to about 40 pbw, more typically from about 0.5 to about 30 pbw, oils.

In one embodiment of the personal care composition of the present invention, the benefit agent comprises a humectant and one or more oils.

In one embodiment, the personal care composition comprises, in each case based on 100 pbw of the composition, from about 50 to less than 100 pbw, more typically from about 70 to about 99 pbw of an aqueous structured surfactant phase comprising an aqueous structured surfactant composition according to the present invention, as described above, and from greater than 0 to about 50 pbw, more typically from about 1 to about 30 pbw, a discontinuous water insoluble or partially water soluble phase dispersed in the aqueous structured surfactant phase.

In one embodiment, the water insoluble or partially water soluble phase comprises an oil.

Oils suitable as a benefit agent and/or as a component of a water insoluble or partially water soluble phase include vegetable oils, such as arachis oil, castor oil, cocoa butter, coconut oil, corn oil, cotton seed oil, olive oil, palm kernel oil, rapeseed oil, sunflower oil, safflower seed oil, sesame seed oil, and soybean oil, shea butter, avocado oil, rice bran oil, jojoba oil, grape seed oil, sweet almond oil, canola oil, apricot oil, walnut oil, and wheat germ oil, mineral oils, such as petrolatum, and silicone oils, such as polydimethylsiloxane.

In one embodiment, the composition of the present invention comprises a humectant, more typically, glycerin, and an oil, more typically a vegetable oil and/or petrolatum.

In one embodiment, the personal care composition of the present invention provides enhanced oil deposition onto the skin or hair.

In one embodiment, the personal care composition of the present invention comprises, in each case based on 100 pbw of the composition:
(a) from about 50 to less than 100 pbw, more typically from about 70 to about 99 pbw, of an aqueous structured surfactant phase, said structured surfactant phase comprising:
  (i) from greater than 0 to about 15 pbw, more typically from about 0.5 to about 10 pbw, and still more typically from about 1 to about 8 pbw, of an alkyl ether sulfate surfactant comprising one or more compounds according to structure (I)

wherein
  $R^1$ is $(C_8\text{-}C_{18})$alkyl,
  m is 2 or 3,
  n is an integer of from 1 to about 5 and
  $X^+$ is a cation.
  (ii) from greater than 0 to about 15 pbw, more typically from about 1.5 to about 12 pbw, and still more typically from about 3 to about 10 pbw, of an alkyl sulfate surfactant comprising one or more compounds according to structure (II):

wherein:
  $R^2$ is $(C_8\text{-}C_{18})$alkyl, and
  $X^+$ is a cation,
  (iii) from greater than 0 to about 10 pbw, more typically from about 0.5 to about 6 pbw, and still more typically from about 1 to about 4 pbw, of an alkanolamide surfactant comprising one or more compounds according to structure (III):

wherein:
  $R^3$ is $(C_5\text{-}C_{24})$ saturated or unsaturated, straight chain or branched aliphatic group,
  $R^4$ and R5 are the same or different, $C_2\text{-}C_4$ straight chain or branched aliphatic groups,
  x is an integer from 0 to 10, y is an integer from 1 to 10, and the sum of x and y is less than or equal to 10, and
  (iv) from 0 to about 10 pbw, more typically from about 1 to about 8 pbw, and still more typically from about 2 to about 6 pbw, of an amphoteric surfactant comprising one or more compounds selected from compounds according to structures (IV) and (V):

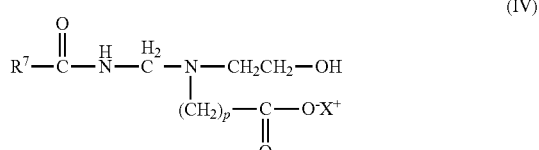

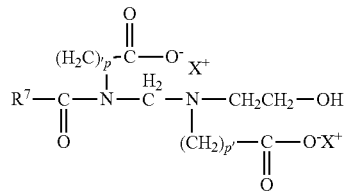

wherein:
$R^6$ is $(C_1\text{-}C_{18})$aliphatic,
p is 2 or 3,
$R^7$ is $(C_1\text{-}C_{18})$aliphatic,
p' is 2 or 3, and
each $X+$ is independently a cation,
provided that the total amount of components (i), (ii), (iii), and (iv) is greater than or equal to 5 pbw, more typically greater than or equal to about 10 pbw, and still more typically greater than or equal to about 15 pbw, of the composition,
  (v) an amount of electrolyte effective to, in combination with components (i), (ii), (ii), and (iv), provide a structured surfactant composition having an opaque visual appearance and exhibiting a yield strength of greater than 0 Pascals, and
  (vi) water, and
(b) from greater than 0 to about 50 pbw, more typically from about 1 to about 30 pbw of a discontinuous water insoluble or partially water soluble phase that comprises one or more oils selected from vegetable oils and is dispersed in the aqueous structured surfactant phase.

In one embodiment, the personal composition is a skin care composition and comprises, based on 100 pbw of the composition, from about 50 to less than 100 pbw, more typically from about 70 to about 99 pbw, and even more typically from about 80 to about 95 pbw, of the aqueous structured surfactant phase, and from greater than 0 to about 50 pbw, more typically from about 1 to about 30 pbw, and even more typically from about 5 to about 20 pbw, of the discontinuous water insoluble or partially water soluble phase.

In another embodiment, the personal care composition of the present invention is a hair care composition and comprises, based on 100 pbw of the composition, from about 85 to less than 100 pbw, more typically from about 90 to about 99 pbw, and even more typically from about 95 to about 99 pbw, of the aqueous structured surfactant phase, and from greater than 0 to about 15 pbw, more typically from about 1 to about 10 pbw, and even more typically from about 1 to about 5 pbw of the discontinuous water insoluble or partially water soluble phase.

The structured surfactant compositions of the invention provide a stable structured composition having non-zero yield strength even in the absence of a polymer thickener.

In some applications, a polymeric thickener may be perceived as imparting an undesirably sticky skin feel to the composition and it is preferred that polymer not be included in the composition or that the amount of polymer be minimized. In one embodiment, the personal care composition is free of polymeric thickeners.

In some applications, the presence of a polymer thickener is not objectionable and in one embodiment the personal care composition of the present invention further comprises, based on 100 pbw of the composition, up to about 5 pbw, more typically up to about 2 pbw, of a polymeric thickener. Suitable polymeric thickeners are compounds known in the art and include, for example, agars, alginates, arabinoxylans, carrageenans, gelatins, gellans, β-glucans, gum arabic, locust bean gums, pectins, succinoglycans, xanthan gums, guars, guar derivatives, such as hydroxypropyl guars (such as Jaguar™ HP-8 guar, Jaguar HP-105 guar, Jaguar HP-60 guar, Jaguar HP-120 guar, Jaguar C-162 guar, each available from Rhodia Inc.) and cationic guars (such as Jaguar C-17 guar, Rhodia Inc.), starches, starches and starch derivatives such as sodium hydroxypropyl starch phosphate (Pure-Gel 980 and Pure-Gel 998 starches, each available from Grain Processing Corporation), cellulose and cellulose derivatives, such as carboxyalkyl celluose, hydroxyalkyl cellulose alkyl cellulose, quaternary ammonium derivatives of hydroxyethylcellulose, acrylate polymers, such as acrylate/aminoacrylate/$C_{10-30}$ alkyl PEG-20 itaconate copolymer (such as Structure-Plus™ polymer from National Starch), cationic polymers (such as Rheovis CSP, Rheovis CDE, and Rheovis CDP polymers from Ciba), polyacrylimidomethylpropane sulfonate/such as polyquaternium-4 (Plexagel™ ASC polymer from ISP), hydrohobically modified nonionic polyols (such as Acusol™ 880 and Acusol 882 polyols from Rohm & Haas), and PEG-150 Distearate.

In one embodiment the personal care composition of the present invention comprises from greater than 0 to about 5 pbw, more typically from about 0.1 to about 2 pbw of one or more polymeric thickeners, more typically one or more polysaccharide polymeric thickeners.

In one embodiment of the personal care composition of the present invention, the benefit agent comprises, based on 100 pbw of the composition, from greater than 0 to about 25 pbw, more typically from about 0.5 to about 20 pbw, humectant, more typically glycerin, and the composition further comprises, based on 100 pbw of the composition from greater than 0 to about 5 pbw, more typically from about 0.1 to about 2 pbw of one or more polymeric thickeners, more typically one or more polysaccharide polymeric thickeners.

In one embodiment, the composition of the present invention comprises a polymeric thickener component that comprises, based on 100 pbw of the composition, from greater than 0 to about 1.5 pbw, more typically from about 0.1 to about 0.5 pbw, cationic guar and from greater than 0 to about 2 pbw, more typically from about 0.1 to about 1.0 pbw, non-derivatized guar.

In those embodiments of the personal care composition according to the present invention that further comprise an optional polymer component, the polymer provides increased viscosity and may provide improved stability and increase the yield strength of the structured surfactant composition compared to an analogous composition that lacks the polymer.

The personal care composition according to the present invention may optionally further comprise, based on 100 pbw of the personal care composition and independently for each such ingredient, from about 0 to about 10 pbw, typically from 0.5 pbw to about 5.0 pbw, of other ingredients known in the art, such as, for example, preservatives such as benzyl alcohol, methyl paraben, propyl paraben and imidazolidinyl urea, electrolytes, such as sodium chloride, sodium sulfate, polyvinyl alcohol, and sodium citrate; pH adjusting agents such as citric acid, succinic acid, phosphoric acid, sodium hydroxide, sodium carbonate; dyes, and sequestering agents such as disodium ethylenediamine tetra-acetate.

In one embodiment, the personal care composition of the present invention comprises a structured surfactant component according to the present invention that forms a first macroscopic "phase" (which may itself comprise a plurality of phases, including aqueous phases, planar lamellar surfactant phases and spherulitic lamellar surfactant phases, as discussed above) and the composition further comprises one or more additional macroscopic phases that are at least substantially distinct from such first phase. As used herein in reference to the phases of a multiphase embodiments of the present invention, the terminology "substantially distinct" means that the phases each exhibit substantially homogeneous properties within a given phase and that the phases differ with respect to at least one characteristic or property, such as for example, visual characteristics, such as color, clarity, pearlescence, or physical/chemical properties, such as viscosity, lubricity, and/or benefit agent content.

The structured surfactant composition of the present application and its use as the structured surfactant phase of the personal care composition of the present application provides good foaming performance in the presence of oil, provides good deposition of oil onto skin and/or hair and enables high loading of the oil phase without requiring the presence of a polymer component.

EXAMPLES A1 to A27

The composition of Examples A1 to A27 were by combining the listed ingredients to provide the relative amounts set forth below in TABLES A-I-A-III.

| | |
|---|---|
| Sodium trideceth sulfate, 3 moles ethoxylation per mole | STES |
| Sodium lauryl sulfate, | SLS |
| Ammonium lauryl sulfate, | ALS |
| Sodium lauroamphoacetate, | SLAA |
| Coco monoethanolamide, | CMEA |
| Sodium chloride, | NaCl |
| Ammonium chloride, | $NH_4Cl$ |
| Citric acid, added as 50% aqueous solution | 50% Citric acid |

Each of the compositions of Examples A1- A27 was evaluated visually to determine the visual appearance, the apparent number of distinct macroscopic phases, the apparent presence of a yield strength, as indicated by the ability to suspend air bubbles in the composition. Compositions which exhibited a single opaque phase that appeared to exhibit a yield strength were judged to be spherulitic compositions. In each case, a positive finding is indicated in the TABLE as a "+" and "NR" indicates that the result of that evaluation is not reported for that Example.

TABLE A-I

| Ingredient | EX A1 | EX A2 | EX A3 | EX A4 | EX A5 | EX A6 | EX A7 | EX A8 | EX A9 |
|---|---|---|---|---|---|---|---|---|---|
| Total Surfactant (%) | 31.6 | 27.7 | 18.9 | 14.2 | 14.0 | 13.7 | 11.0 | 9.3 | 9.0 |
| STES (%) | 10.2 | 9.0 | 6.1 | 4.6 | 4.5 | 4.4 | 3.6 | 3.0 | 2.9 |
| SLS (%) | 10.2 | 9.0 | 6.1 | 4.6 | 4.5 | 4.4 | 3.6 | 3.0 | 2.9 |

TABLE A-I-continued

| Ingredient | EX A1 | EX A2 | EX A3 | EX A4 | EX A5 | EX A6 | EX A7 | EX A8 | EX A9 |
|---|---|---|---|---|---|---|---|---|---|
| SLAA (%) | 6.8 | 6.0 | 4.1 | 3.1 | 3.0 | 3.0 | 2.4 | 2.0 | 1.9 |
| CMEA (%) | 4.3 | 3.8 | 2.6 | 1.9 | 1.9 | 1.9 | 1.5 | 1.3 | 1.2 |
| NaCl (%) | 0 | 11.9 | 41 | 1.5 | 3.0 | 4.4 | 2.4 | 0 | 3.8 |
| Water (%) | 68.5 | 60.3 | 77.0 | 84.3 | 83.1 | 81.8 | 86.6 | 90.7 | 87.2 |
| Opaque? | NR | + | + | NR | + | + | NR | − | + |
| # Phase(s) | 2 | 1 | 1 | 2 | 1 | 1 | 2 | 1 | 1 |
| Yield Strength? | NR | + | + | NR | + | + | NR | − | + |
| Spherulitic? | − | + | + | − | + | + | − | − | + |

TABLE A-II

| Ingredient | EX A10 | EX A11 | EX A12 | EX A13 | EX A14 | EX A15 | EX A16 | EX A17 | EX A18 |
|---|---|---|---|---|---|---|---|---|---|
| Total Surfactant (%) | 14.0 | 11.0 | 18.9 | 13.7 | 14.2 | 9.0 | 9.3 | 27.7 | 31.5 |
| STES (%) | 2.3 | 1.8 | 3.1 | 2.2 | 2.3 | 1.4 | 1.5 | 4.5 | 5.1 |
| SLS (%) | 6.8 | 5.4 | 9.2 | 6.7 | 6.9 | 4.3 | 4.5 | 13.5 | 15.3 |
| SLAA (%) | 3.0 | 2.4 | 4.1 | 3.0 | 3.1 | 1.9 | 2.0 | 6.0 | 6.8 |
| CMEA (%) | 1.9 | 1.5 | 2.6 | 1.9 | 1.9 | 1.2 | 1.3 | 3.8 | 4.3 |
| NaCl (%) | 3.0 | 2.4 | 4.1 | 4.4 | 1.5 | 3.8 | 0.0 | 11.9 | 0.0 |
| Water (%) | 83.1 | 86.6 | 77.0 | 81.8 | 84.3 | 87.2 | 90.7 | 60.4 | 68.5 |
| Opaque? | + | + | + | + | − | + | − | NR | NR |
| # Phases | 1 | 1 | 1 | 1 | 1 | 1 | 1 | 2 | 2 |
| Yield Strength? | + | − | + | + | − | + | − | NR | NR |
| Spherulitic? | + | − | + | + | − | + | − | − | − |

TABLE A-III

| Ingredient | EX A19 | EX A20 | EX A21 | EX A22 | EX A23 | EX A24 | EX A25 | EX A26 | EX A27 |
|---|---|---|---|---|---|---|---|---|---|
| Total Surfactant (%) | 14.0 | 11.0 | 18.9 | 13.7 | 14.2 | 9.0 | 9.3 | 27.7 | 31.5 |
| STES (%) | 4.5 | 3.6 | 6.1 | 4.4 | 4.6 | 2.9 | 3.0 | 9.0 | 10.2 |
| ALS (%) | 4.5 | 3.6 | 6.1 | 4.4 | 4.6 | 2.9 | 3.0 | 9.0 | 10.2 |
| SLAA (%) | 3.0 | 2.4 | 4.1 | 3.0 | 3.1 | 1.9 | 2.0 | 6.0 | 6.8 |
| CMEA (%) | 1.9 | 1.5 | 2.6 | 1.9 | 1.9 | 1.2 | 1.3 | 3.8 | 4.3 |
| NaCl (%) | 3.0 | 2.4 | 4.1 | 4.4 | 1.5 | 3.8 | 0.0 | 11.9 | 0.0 |
| Water (%) | 83.1 | 86.6 | 77.0 | 81.8 | 84.3 | 87.2 | 90.7 | 60.4 | 68.5 |
| Opaque? | NR | NR | + | + | NR | + | − | + | NR |
| # Phases | 2 | 2 | 1 | 1 | 2 | 1 | 1 | 1 | 2 |
| Yield Strength? | NR | NR | + | + | NR | + | − | + | NR |
| Spherulitic? | − | − | + | + | − | + | − | + | − |

EXAMPLES B1 TO B24

The composition of Examples B1 to B24 were made by combining the listed ingredients to provide the relative amounts set forth below in TABLES B-I to B-III and were evaluated with respect to visual appearance, the apparent number of distinct macroscopic phases, the apparent presence of a yield strength, in the same manner as described above in regard to Examples A1-A27.

TABLE B-I

| Ingredient | B1 | B2 | B3 | B4 | B5 | B6 | B7 | B8 |
|---|---|---|---|---|---|---|---|---|
| STES (%) | 2.84 | 2.81 | 2.79 | 2.76 | 2.84 | 2.81 | 2.79 | 2.76 |
| SLS (%) | 5.66 | 5.61 | 5.55 | 5.50 | 5.66 | 5.61 | 5.55 | 5.50 |
| SLAA (%) | 3.82 | 3.78 | 3.74 | 3.71 | 3.82 | 3.37 | 2.35 | 2.33 |
| CMEA (%) | 2.39 | 2.37 | 2.35 | 2.33 | 2.39 | 2.37 | 2.35 | 2.33 |
| NaCl (%) | 1.96 | 2.91 | 3.85 | 4.76 | 0.00 | 0.00 | 0.00 | 0.00 |
| NH$_4$Cl (%) | 0.00 | 0.00 | 0.00 | 0.00 | 1.96 | 1.75 | 1.73 | 1.71 |
| Water (%) | 81.56 | 80.77 | 79.99 | 79.23 | 81.56 | 80.77 | 79.99 | 79.23 |
| Opaque? | NR | + | + | + | + | + | + | + |
| # Phases | 2 | 1 | 1 | 1 | 1 | 1 | 1 | 1 |
| Yield Strength? | NR | + | + | + | + | + | + | + |
| Spherulitic? | − | + | + | + | + | + | + | + |

TABLE B-II

| Ingredient | B9 | B10 | B11 | B12 | B13 | B14 | B15 | B16 |
|---|---|---|---|---|---|---|---|---|
| STES (%) | 3.79 | 3.75 | 3.72 | 3.68 | 4.85 | 4.80 | 4.75 | 4.71 |
| SLS (%) | 7.55 | 7.48 | 7.41 | 7.34 | 4.85 | 4.80 | 4.75 | 4.71 |
| SLAA (%) | 5.09 | 5.04 | 4.99 | 4.94 | 3.26 | 3.22 | 3/19 | 3/16 |
| CMEA (%) | 3.19 | 3.16 | 3.13 | 3.10 | 2.02 | 2.02 | 2.00 | 1.98 |
| NaCl (%) | 0.00 | 0.00 | 0.00 | 0.00 | 0.00 | 0.99 | 1.95 | 2.91 |
| NH$_4$Cl (%) | 1.96 | 2.91 | 3.85 | 4.76 | 0.00 | 0.00 | 0.00 | 0.00 |
| % 0% Citric acid | 1.76 | 1.75 | 1.73 | 1.71 | 1.80 | 1.78 | 1.76 | 1.73 |
| Water (%) | 76.65 | 75.91 | 75.18 | 74.46 | 83.20 | 82.38 | 81.57 | 80.78 |
| Opaque? | + | + | + | + | − | − | NR | + |
| # Phases | 1 | 1 | 1 | 1 | 1 | 1 | 2 | 1 |
| Yield Strength? | + | + | + | + | − | − | NR | + |
| Spherulitic? | + | + | + | + | − | − | − | + |

TABLE B-III

| Ingredient | B17 | B18 | B19 | B20 | b21 | B22 | B23 | B24 |
|---|---|---|---|---|---|---|---|---|
| STES (%) | 4.66 | 4.62 | 6.47 | 6.40 | 6.34 | 6.28 | 6.22 | 6.16 |
| SLS (%) | 4.66 | 4.62 | 6.47 | 6.40 | 6.34 | 6.28 | 6.22 | 6.16 |
| SLAA (%) | 3.13 | 3.10 | 4.34 | 4.30 | 4.26 | 4.21 | 4.17 | 4.13 |
| CMEA (%) | 1.96 | 1.95 | 2.72 | 2.70 | 2.67 | 2.64 | 2.62 | 2.59 |
| NaCl (%) | 3.85 | 4.76 | 0.00 | 0.99 | 1.96 | 2.91 | 3.85 | 4.76 |
| NH$_4$Cl | 0.00 | 0.00 | 0.00 | 0.00 | 0.00 | 0.00 | 0.00 | 0.00 |
| 50% Citric acid | 1.73 | 1.71 | 1.80 | 1.78 | 1.76 | 1.75 | 1.73 | 1.71 |
| Water (%) | 80.00 | 79.24 | 78.20 | 77.43 | 76.67 | 75.93 | 75.20 | 74.46 |
| Opaque? | + | + | − | NR | + | + | + | + |
| # Phases | 1 | 1 | 1 | 2 | 1 | 1 | 1 | 1 |
| Yield Strength? | + | + | − | NR | + | + | + | + |
| Spherulitic? | + | + | − | − | + | + | + | + |

The yield strength of some of the compositions was determined by measuring the stress as a function of shear rate, typically at shear rates from 0.1 s-1 to 500 s-1, using a AR-G2 Rheometer from TA Instruments. The composition of Example B3 exhibited a yield strength of 5.264 Pa and the composition of Example B6 exhibited a yield strength of 1.403 Pa.

EXAMPLES C1 to C14

The personal care compositions of Examples C1 to C14 were made by combining the listed ingredients to provide a composition comprising the amounts indicated, as pbw per 100 pbw composition.

All compositions provided opaque, white, viscous creamy compositions, useful as moisturizing body wash compositions.

TABLE C1

| Ingredient | EX C1 | EX C2 | EX C3 | EX C4 | EX C5 | EX C6 |
|---|---|---|---|---|---|---|
| Water | 64.54 | 68.57 | 80.69 | 64.20 | 75.56 | 67.82 |
| STES | 2.90 | 2.34 | 2.75 | 3.10 | 3.65 | 3.87 |
| SLS | 5.77 | 4.66 | 5.48 | 6.18 | 7.28 | 3.87 |
| SLAA | 3.89 | 3.14 | 3.69 | 4.16 | 4.90 | 2.60 |
| CMEA | 2.44 | 1.97 | 2.32 | 2.61 | 3.08 | 1.63 |
| Sunflower Oil | 15.00 | 0 | 0 | 0 | 0 | 0 |
| Jaguar C-17 | 0.20 | 0.20 | 0.20 | 0.20 | 0.20 | 0.20 |
| Rapeseed Oil | 0 | 15.00 | 0 | 15.00 | 0 | 15.00 |
| Jaguar S | 0.50 | 0 | 0 | 0 | 0 | 0 |
| NH$_4$Cl | 3.50 | 2.87 | 3.37 | 2.87 | 3.37 | 0 |
| NaCl | 0 | 0 | 0 | 0 | 0 | 3.65 |
| Citric acid (50% soln) | 1.26 | 1.26 | 1.48 | 1.67 | 1.96 | 1.36 |
| Total | 100.00 | 100.00 | 100.00 | 100.00 | 100.00 | 100.00 |

TABLE C2

| Ingredient | EX C7 | EX C8 | EX C9 | EX C10 | EX C11 | EX C12 |
|---|---|---|---|---|---|---|
| Water | 79.82 | 64.76 | 76.22 | 64.54 | 67.56 | 79.51 |
| STES | 4.55 | 5.23 | 6.16 | 2.42 | 1.93 | 2.27 |
| SLS | 4.55 | 5.23 | 6.16 | 7.28 | 5.79 | 6.81 |
| SLAA | 3.06 | 3.51 | 4.14 | 3.26 | 2.59 | 3.05 |
| CMEA | 1.92 | 2.20 | 2.59 | 2.04 | 1.62 | 1.91 |
| Jaguar C-17 | 0.20 | 0.20 | 0.20 | 0.20 | 0.20 | 0.20 |
| Jaguar S | 0 | 0 | 0 | 0.50 | 0 | 0 |
| Rapeseed Oil | 0 | 15.00 | 0 | 0 | 15.00 | 0 |
| Sunflower Oil | 0 | 0 | 0 | 15.00 | 0 | 0 |
| NaCl | 4.30 | 2.47 | 2.91 | 0 | 0 | 0 |
| NH$_4$Cl | 0 | 0 | 0 | 5.00 | 4.04 | 4.75 |
| Citric acid (50% soln) | 1.60 | 1.38 | 1.62 | 1.26 | 1.27 | 1.50 |
| Total | 100.00 | 100.00 | 100.00 | 100.00 | 100.00 | 100.00 |

TABLE C3

| Ingredient | EX C13 | EX C14 |
|---|---|---|
| Water | 64.07 | 75.40 |
| STES | 2.59 | 3.05 |
| SLS | 7.77 | 9.15 |
| SLAA | 3.48 | 4.09 |
| Cocamide MEA | 2.18 | 2.57 |
| Rapeseed Oil | 15.00 | 0 |
| Jaguar C-17 | 0.20 | 0.20 |
| NH$_4$Cl | 3.26 | 3.84 |
| Citric acid (50% soln) | 1.44 | 1.70 |
| Total | 100.00 | 100.00 |

The yield strength of some of the compositions was measured using the method described above in regard to the compositions of Examples B3 and B6. The composition of Example C1 exhibited a yield strength of 5.556 Pa and the composition of Example C2 exhibited a yield strength of 4.43 Pa.

The invention claimed is:

1. A structured surfactant composition, comprising, based on 100 parts by weight of said composition:

(i) from about 0.5 to about 10 parts by weight of an alkyl ether sulfate surfactant comprising one or more compounds according to structure (I):

  (I)

wherein
R$^1$ is tridecyl,
m is 2 or 3,
n is an integer of from 1 to about 5 and
X$^+$ is a cation, (ii) from about 1.5 to about 12 parts by weight of an alkyl sulfate surfactant comprising one or more compounds according to structure (II):

  (II)

wherein:
R$^2$ is (C$_8$-C$_{18}$)alkyl, and
X$^+$ is a cation, (iii) from about 0.5 to about 6 parts by weight of an alkanolamide surfactant comprising one or more compounds according to structure (III):

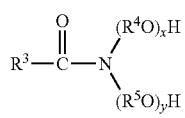  (III)

wherein:
R$^3$ is (C$_5$-C$_{24}$) saturated or unsaturated, straight chain or branched aliphatic group,
R$^4$ and R5 are the same or different, C$_2$-C$_4$ straight chain or branched aliphatic groups,
x is an integer from 0 to 10, y is an integer from 1 to 10, and the sum of x and y is less than or equal to 10, and (iv) from 0 to about 8 parts by weight of an amphoteric surfactant comprising one or more compounds selected from compounds according to structures (IV) and (V):

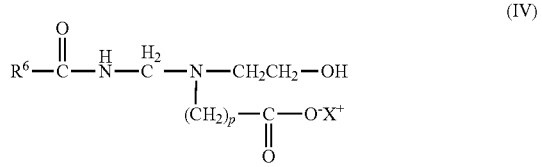  (IV)

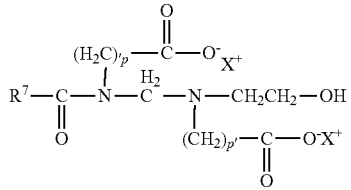  (V)

wherein:
R$^6$ is (C$_1$-C$_{18}$)aliphatic, p is 2 or 3, and
R$^7$ is (C$_1$-C$_{18}$)aliphatic, p' is 2 or 3, and each X+ is independently a cation, provided that the total amount of components (i), (ii), (iii), and (iv) is greater than or equal to 5 parts by weight of the composition, (v) an amount of electrolyte effective to, in combination with components (i), (ii), (iii), and (iv) and in the absence of a polymer thickener, provide a liquid crystalline structured surfactant composition having an opaque visual appearance and exhibiting a yield strength of greater than 0 Pascals, and (vi) water.

2. The composition of claim 1, wherein the composition is a personal care composition.

3. The composition of claim 1, wherein the composition further comprises a personal care benefit agent.

4. The composition of claim 3, wherein the benefit agent comprises one or more of oils, emollients, moisturizers, humectants, conditioners, polymers, vitamins, abrasives, UV absorbers, antimicrobial agents, anti-dandruff agents, fragrances, and appearance modifying additives.

5. The composition of claim 4, wherein the benefit agent comprises a humectant.

6. The composition of claim 5, wherein the composition further comprises one or more polymeric thickeners.

7. The composition of claim 5, wherein the composition further comprises one or more oils.

8. A composition, comprising, based on 100 parts by weight of the composition:
(a) from about 50 to less than 100 parts by weight of an aqueous structured surfactant phase, said structured surfactant phase comprising a structured surfactant composition according to claim 1, and
(b) from greater than 0 to about 50 parts by weight of a discontinuous water insoluble or partially water soluble phase dispersed in the aqueous structured surfactant phase.

9. The composition of claim 8, wherein the water insoluble or partially water soluble phase comprises an oil.

10. The composition of claim 9, wherein water insoluble or partially water soluble phase comprises one or more of vegetable oils, mineral oils, and silicone oils.

11. The composition of claim 10, wherein water insoluble or partially water soluble phase comprises one or more vegetable oils selected from arachis oil, castor oil, cocoa butter, coconut oil, corn oil, cotton seed oil, olive oil, palm kernel oil, rapeseed oil, sunflower oil, safflower seed oil, sesame seed oil, and soybean oil, shea butter, avocado oil, rice bran oil, jojoba oil, grape seed oil, sweet almond oil, canola oil, apricot oil, walnut oil, and wheat germ oil.

12. The composition of claim 10, wherein water insoluble or partially water soluble phase comprises petrolatum.

* * * * *